US011179061B1

(12) United States Patent
Hummer

(10) Patent No.: US 11,179,061 B1
(45) Date of Patent: Nov. 23, 2021

(54) METHOD AND DEVICES FOR DETECTING VIRUSES AND BACTERIAL PATHOGENS

(71) Applicant: Gregory J. Hummer, Shaker Heights, OH (US)

(72) Inventor: Gregory J. Hummer, Shaker Heights, OH (US)

(*) Notice: Subject to any disclaimer, the term of this patent is extended or adjusted under 35 U.S.C. 154(b) by 0 days.

(21) Appl. No.: 16/926,701

(22) Filed: Jul. 11, 2020

(51) Int. Cl.
*A61B 5/097* (2006.01)
*A61B 5/08* (2006.01)
*C12Q 1/6825* (2018.01)
*A61B 5/00* (2006.01)
*G01N 33/497* (2006.01)

(52) U.S. Cl.
CPC ............ *A61B 5/097* (2013.01); *A61B 5/082* (2013.01); *C12Q 1/6825* (2013.01); *C12Q 2565/607* (2013.01); *G01N 33/497* (2013.01)

(58) Field of Classification Search
CPC ...... A61B 5/097; A61B 5/082; C12Q 1/6825; C12Q 1/68; C12Q 2565/607; C12Q 2565/60; C12Q 2565/00; G01N 33/497; G01N 33/483; G01N 33/48
USPC ................................. 600/532; 436/900, 149
See application file for complete search history.

(56) References Cited

U.S. PATENT DOCUMENTS

| 9,643,186 B1* | 5/2017 | Ahmad | .................... B01L 3/561 |
| 2007/0189921 A1* | 8/2007 | Duong | ............... G01N 21/6452 436/149 |
| 2019/0046092 A1* | 2/2019 | LaBelle | ............... A61B 5/4839 |

FOREIGN PATENT DOCUMENTS

| WO | WO- 2017/055229 A1 * | 4/2017 | .......... G01N 33/543 |
| WO | 2018/075085 A1 | 4/2018 | |

* cited by examiner

*Primary Examiner* — Christine T Mui
(74) *Attorney, Agent, or Firm* — Edmond DeFrank

(57) ABSTRACT

The embodiments disclose a method including making electrodes using an electrically conductive material for impedimetric detection of analytical targets in an electrochemical sensing platform device, collecting patient samples in a solution compartment of the electrochemical sensing platform device, binding primers and aptamers to electrodes for functionalizing electrodes for detecting and binding targeted viruses and bacterial pathogens, incubating oral fluid samples in the solution compartment using a heater, measuring electrode impedance changes, recording measured electrode impedance changes in a memory device, and integrating wireless technologies into the electrochemical sensing platform device configured for transmitting recorded measured data.

10 Claims, 21 Drawing Sheets

```
                    ┌──────────────────────────────┐
              1604 ─│ INKJET NOZZLE DEPOSITS AN    │         1613  ┌──────────┐
                    │ ELECTRICALLY CONDUCTIVE      │               │ EXTERNAL │
                    │ ELECTRODE MATERIAL           │               │ POWER    │
                    └──────────────────────────────┘               │ SOURCE   │
1600                             │                                 └──────────┘
┌─────────────────────────────────────────────────────────────────────────────┐
│                                         1640                                │
│  ELECTROCHEMICAL              ┌──────────────────┐                          │
│  DETECTION DEVICE             │   POLYIMIDE      │                          │
│  FOR COVID-19 SARS-           │   FLEXIBLE       │                          │
│  CoV-2 VIRUS IN               │   SUBSTRATE      │                          │
│  SALIVA                 1610  └──────────────────┘                          │
│                                      │                   ┌──────────┐       │
│  ┌──────────────┐              ┌──────────────┐          │ INTERNAL │       │
│  │ DNA PRIMER   │              │ INKJET PRINTED│◄─────── │ POWER    │       │
│  │ COATING      │              │ SENSOR       │          │ SOURCE   │       │
│  │ SPECIFIC FOR │─────────────►│ ELECTRODE    │          └──────────┘       │
│  │ SARS-COV-2 IS│       1615                              1612              │
│  │ BOUND TO THE │      ┌──────────────┐       ┌──────────────┐              │
│  │ ELECTRICALLY │      │ SOLUTION     │◄──────│ INCUBATION   │              │
│  │ CONDUCTIVE   │ 1620 │ COMPARTMENT  │       │ HEATER       │              │
│  │ ELECTRODE    │      └──────────────┘       └──────────────┘              │
│  └──────────────┘                               1614                        │
│                                                                             │
│                                                   ┌──────────┐ 1617         │
│                                                   │ SALIVA   │              │
│                                                   │ SAMPLE   │              │
│                                                   └──────────┘              │
│         ┌──────────────────────────┐                                        │
│  1622 ──│ SARS-CoV-2 IS BOUND      │                                        │
│         │ TO THE ELECTRICALLY      │                                        │
│         │ CONDUCTIVE               │                                        │
│         │ ELECTRODES WITH          │                                        │
│         │ DNA PRIMER               │                                        │
│         └──────────────────────────┘                                        │
│                    │                                                        │
│         ┌──────────────────────────┐                                        │
│         │ IMPEDANCE                │                                        │
│         │ MEASUREMENT              │                                        │
│         └──────────────────────────┘                                        │
│  1650            │                              1670                        │
│         ┌──────────────────────────┐     ┌──────────────┐                   │
│  1660 ──│ WIFI TRANSMISSION        │────►│ SMART PHONE  │                   │
│         │ TO A SMART PHONE         │     └──────────────┘                   │
│         └──────────────────────────┘                                        │
│  1680   ┌────────────────────────────────────────┐                          │
│         │ TESTING RESULTS DISPLAYED              │                          │
│         │ ON A SENSING PLATFORM                  │◄─────                    │
│         │ SMART PHONE APP                        │                          │
│         └────────────────────────────────────────┘                          │
└─────────────────────────────────────────────────────────────────────────────┘
```

METHOD AND DEVICES FOR DETECTING VIRUSES AND BACTERIAL PATHOGENS

BACKGROUND

The recent onset of the Covid-19 pandemic has made apparent a rapid and accurate detection of infection is needed for early treatment and analysis of the rate of spreading of the infections. The rapid and accurate detection of infection is also needed for other known infectious viruses and bacterial pathogens and new infectious viruses and bacterial pathogens that may appear. Initial testing was slow and confined to a small number of laboratories using processes that in many cases took days to complete. What is needed for rapid detection for treatment and to collect ample data to locate and measure the rates of infection is a broader range of application venue availability outside of laboratories and a range of training needed to perform the detection testing.

BRIEF DESCRIPTION OF THE DRAWINGS

FIG. 16 shows a block diagram of an overview of an example of electrode binding of targeted RNA/DNA viruses and bacterial pathogens of one embodiment.

DETAILED DESCRIPTION OF THE INVENTION

In a following description, reference is made to the accompanying drawings, which form a part hereof, and in which is shown by way of illustration a specific example in which the invention may be practiced. It is to be understood that other embodiments may be utilized and structural changes may be made without departing from the scope of the present invention.

General Overview:

It should be noted that the descriptions that follow, for example, in terms of a method and devices for detecting viruses and bacterial pathogens is described for illustrative purposes and the underlying system can apply to any number and multiple types of viruses and bacterial pathogens. In one embodiment of the present invention, the method and devices for detecting viruses and bacterial pathogens can be configured using one or both internal and external power source. The method and devices for detecting viruses and bacterial pathogens can be configured to include a single electrochemical sensing platform device and can be configured to include multiple electrochemical sensing platform devices using the present invention.

Figure 1:
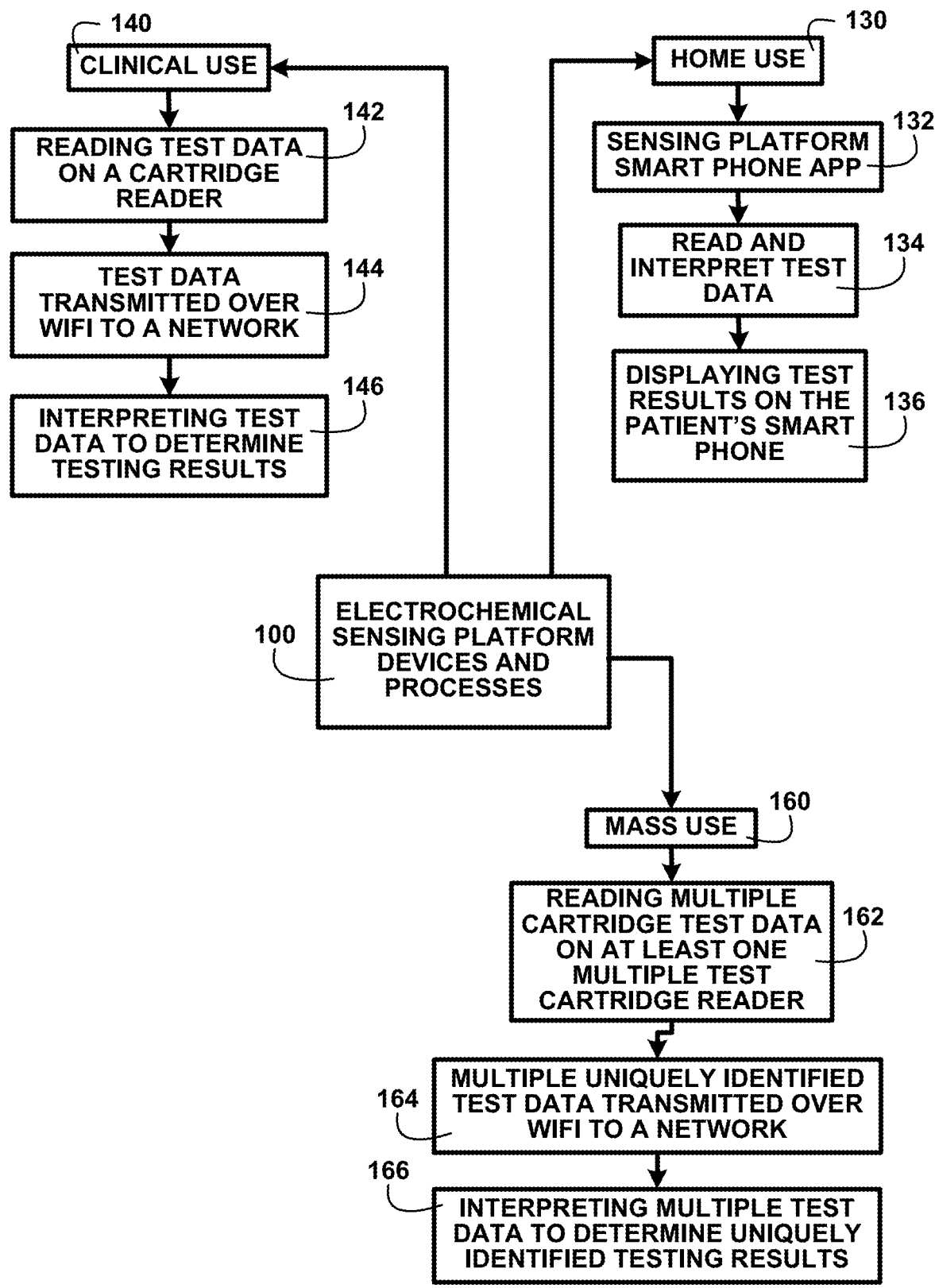
FIG. 1 shows a block diagram of an overview of a method and devices for detecting viruses and bacterial pathogens of one embodiment.

FIG. 1 shows a block diagram of an overview of a method and devices for detecting viruses and bacterial pathogens of one embodiment. FIG. 1 shows electrochemical sensing platform devices and processes 100. The electrochemical sensing platform devices and processes 100 include testing protocol controls for example but not limited to the SARS-CoV-2 virus that causes Covid-19, MRSA, other viruses, and bacteria and pathogens on food.

In one embodiment the electrochemical sensing platform devices and processes 100 are configured for home use 130. The electrochemical sensing platform devices and processes 100 configured for home use 130 performs recording and reading of testing data and interpretation of the test data. The home use 130 patient may view the test results using a sensing platform smart phone app 132 downloaded to the patient's smart phone. The electrochemical sensing platform devices and processes 100 configured for home use 130 using at least one communication devices transmits the results of the read and interpret test data 134 processes to the sensing platform smart phone app 132. The patient sees the sensing platform smart phone app 132 displaying test results on the patient's smart phone 136 of one embodiment.

In another embodiment the electrochemical sensing platform devices and processes 100 are configured for clinical use 140. The test data is processed for reading test data on a cartridge reader 142. Clinical use 140 test data is transmitted over WIFI to a network 144 and is stored on a database. The network processes interpreting test data to determine testing results 146. The testing results are reported to a clinician and attending physician of one embodiment.

In yet another embodiment the electrochemical sensing platform devices and processes 100 are configured for mass use 160. Mass use 160 includes reading multiple cartridge test data on at least one multiple test cartridge reader 162. The multiple uniquely identified test data transmitted over WIFI to a network 164 is recorded on at least one database. The network processes interpreting multiple test data to determine uniquely identified testing results 166. The uniquely identified testing results are reported to a clinician and attending physician of one embodiment.

DETAILED DESCRIPTION

Figure 2:
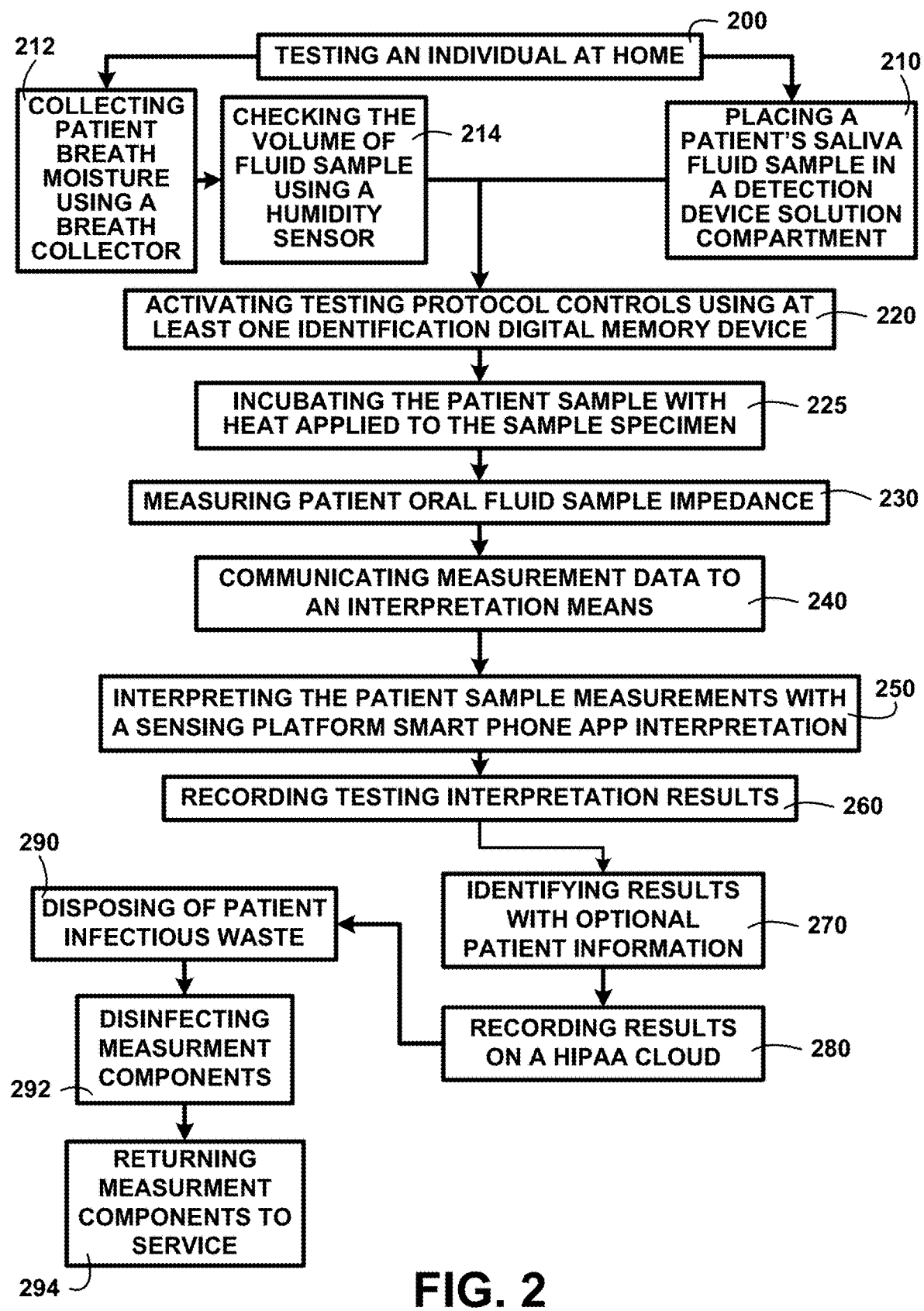
FIG. 2 shows a block diagram of an overview flow chart of testing an individual at home of one embodiment.

FIG. 2 shows a block diagram of an overview flow chart of testing an individual at home of one embodiment. FIG. 2 shows testing an individual at home 200. Testing an individual at home 200 includes placing a patient's saliva fluid sample in a detection device solution compartment 210. In another embodiment a sample is obtained with collecting patient breath moisture using a breath collector 212. The breath collector includes a process of checking the volume of fluid sample using a humidity sensor 214.

The electrochemical sensing platform devices and processes 100 of FIG. 1 are configured for detecting any number and multiple types of viruses and bacterial pathogens using impedimetric detection of analytical targets. The electrochemical sensing platform devices and processes 100 of FIG. 1 include activating testing protocol controls using at least one identification digital memory device 220 for example but not limited to the SARS-CoV-2 virus that causes Covid-19, MRSA, other viruses, and bacteria and pathogens on food. The electrochemical sensing platform devices and processes 100 of FIG. 1 include incubating the patient sample with heat applied to the sample specimen 225. Heated incubation processing prepares the testing for measuring patient oral fluid sample impedance 230. Heated incubation processing prepares the testing for blood and serum for measuring impedance.

The electrochemical sensing platform devices and processes 100 of FIG. 1 include communication devices for communicating measurement data to an interpretation means 240. Processing includes interpreting the patient sample measurements with a sensing platform smart phone app interpretation 250. The sensing platform smart phone interpretation app 250 includes recording testing interpretation results 260. In one embodiment sensing platform smart phone interpretation app 250 includes identifying results with optional patient information 270 and recording results on a HIPAA cloud 280. After the results are determined the processing continues with disposing of patient infectious waste 290, disinfecting measurement components 292, and returning measurement components to service 294 of one embodiment.

Figure 3:
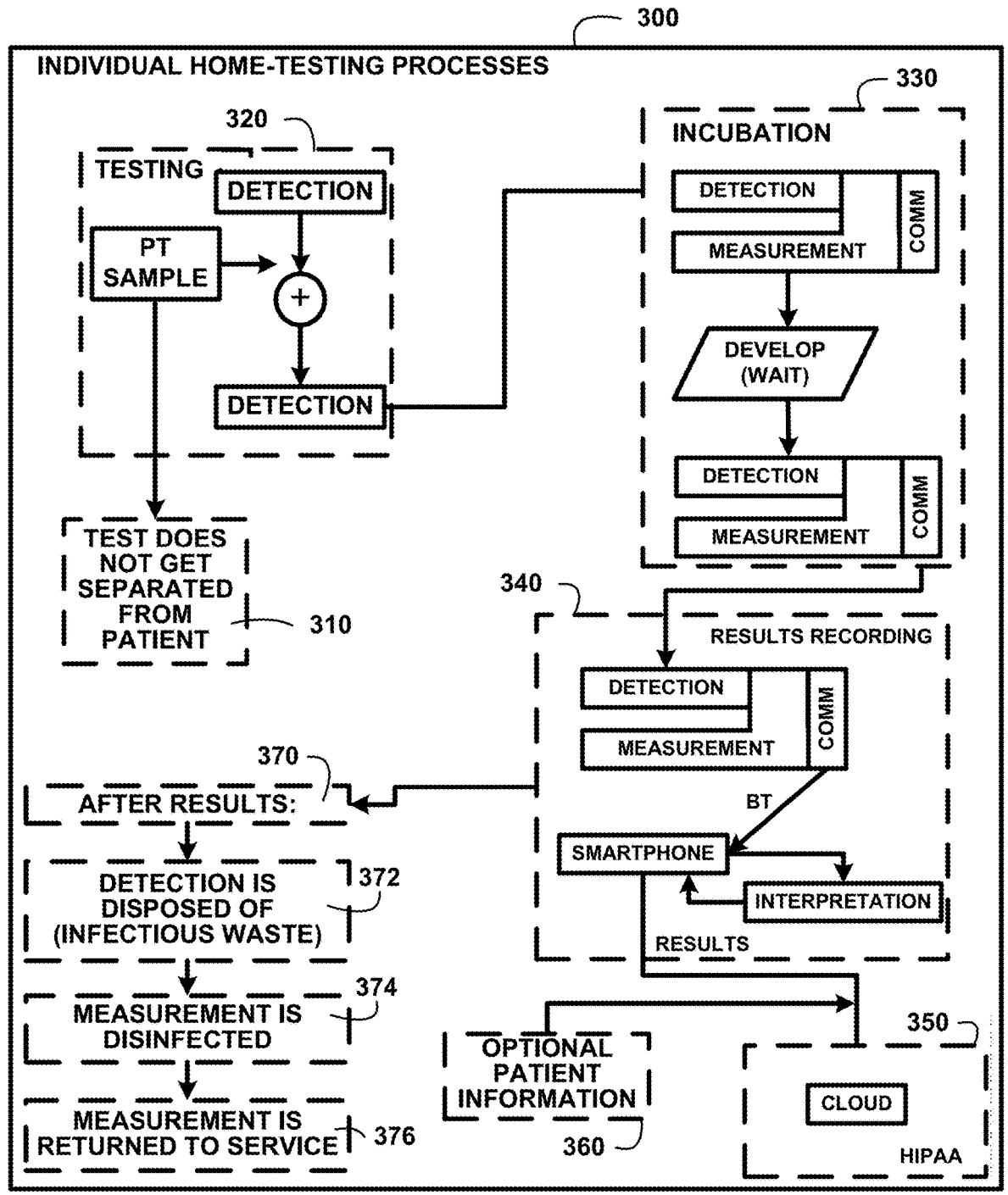
FIG. 3 shows for illustrative purposes only an example of an individual home-testing process of one embodiment.

An Individual Home-Testing Process:

FIG. 3 shows for illustrative purposes only an example of an individual home-testing process of one embodiment. FIG. 3 shows individual home-testing processes 300. The test does not get separated from patient 310. The testing 320 processes include detection prior to placing the patient sample to confirm a clear base. Upon placing the patient sample the detection process continues. A second detection process is conducted and measurement of any changes in the impedance of the detection electrode. The patient sample is processed with incubation 330. A comm device is used to transmit the multiple detection measurements to the sensing platform smart phone app 132 of FIG. 1. During incubation the patient sample is heated over a predetermined time period and at a predetermined heat level to develop the patient sample. After the development period another detection measurement is processed and transmitted over comm.

The results recording 340 will include the detection and measurement. The comm will transmit the detection and measurement data for BT interpretation on the patient smart phone. The results will also be transmitted to a HIPAA cloud 350 and include optional patient information 360. After results: 370 have been recorded devices for detection is disposed of (infectious waste) 372, measurement is disinfected 374 and measurement is returned to service 376 of one embodiment.

Figure 4:
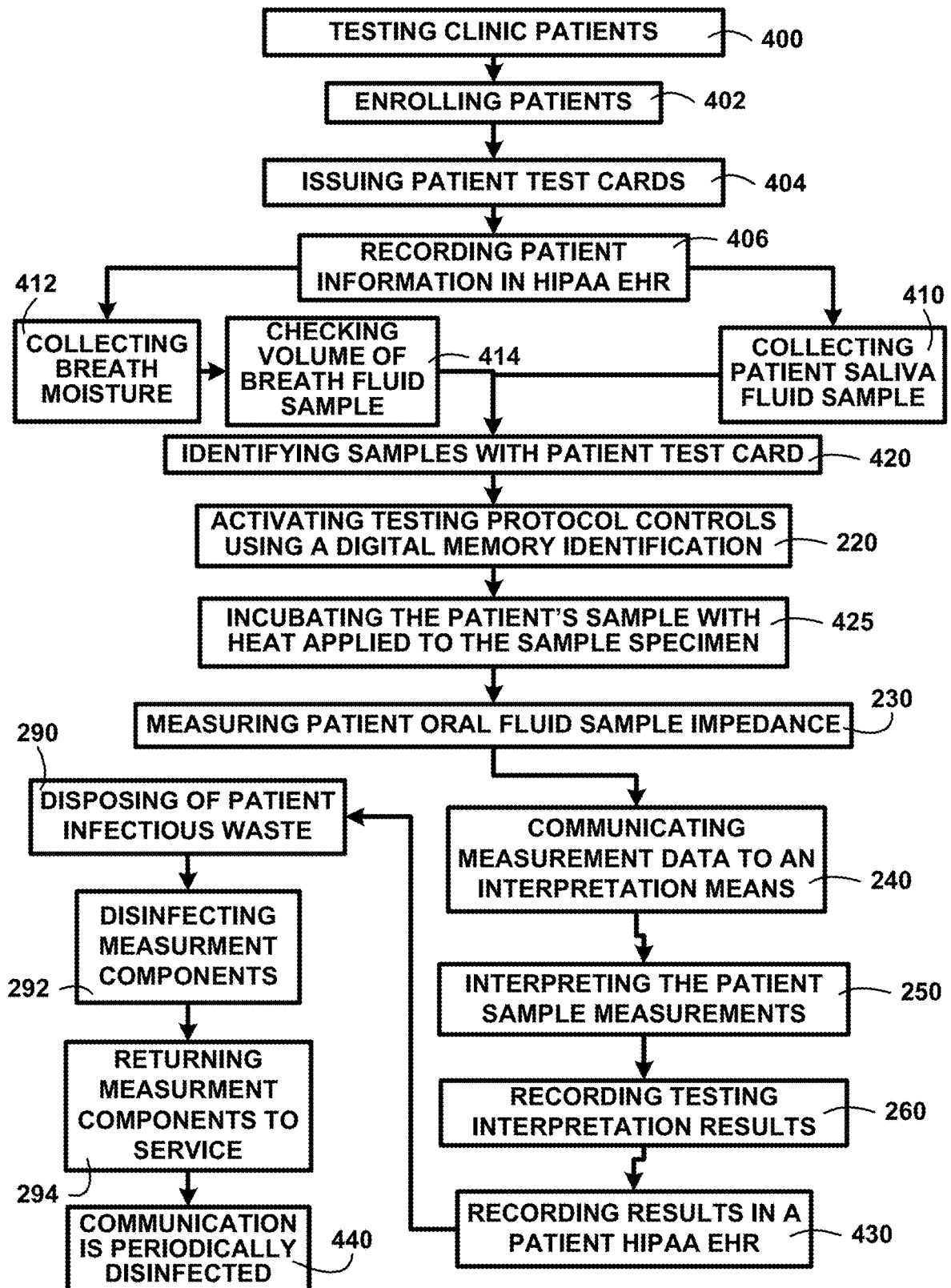
FIG. 4 shows a block diagram of an overview flow chart of testing clinic patients of one embodiment.

Testing Clinic Patients:

FIG. 4 shows a block diagram of an overview flow chart of testing clinic patients of one embodiment. FIG. 4 shows testing clinic patients 400 processing. Testing clinic patients 400 processing begins with enrolling patients 402 and issuing patient test cards 404. The patient test cards include a unique identifying code and patient information. The processing continues with recording patient information in HIPAA EHR 406.

Collecting patient saliva fluid sample 410 for testing. In another embodiment a patient sample includes collecting breath moisture 412 and checking volume of breath fluid sample 414 for a sufficient sample specimen, and may require additional patient exhalations into the device. The process includes identifying samples with patient test card 420. The testing process is prepared with activating testing protocol controls using at least one identification digital memory device 220.

The processing proceeds with incubating the patient's sample with heat applied to the sample specimen 425. When incubation is completed the process continues with measuring patient oral fluid sample impedance 230. The impedance of the electrode is affected by the presence of the incubated patient sample.

Communicating measurement data to an interpretation means 240 for interpreting the patient sample measurements with a sensing platform smart phone app interpretation 250. The process includes recording testing interpretation results 260 and recording results in a patient HIPAA EHR 430. After the results are recorded the process includes disposing of patient infectious waste 290, disinfecting measurement components 292, returning measurement components to service 294 and communication is periodically disinfected 440 of one embodiment.

Figure 5:
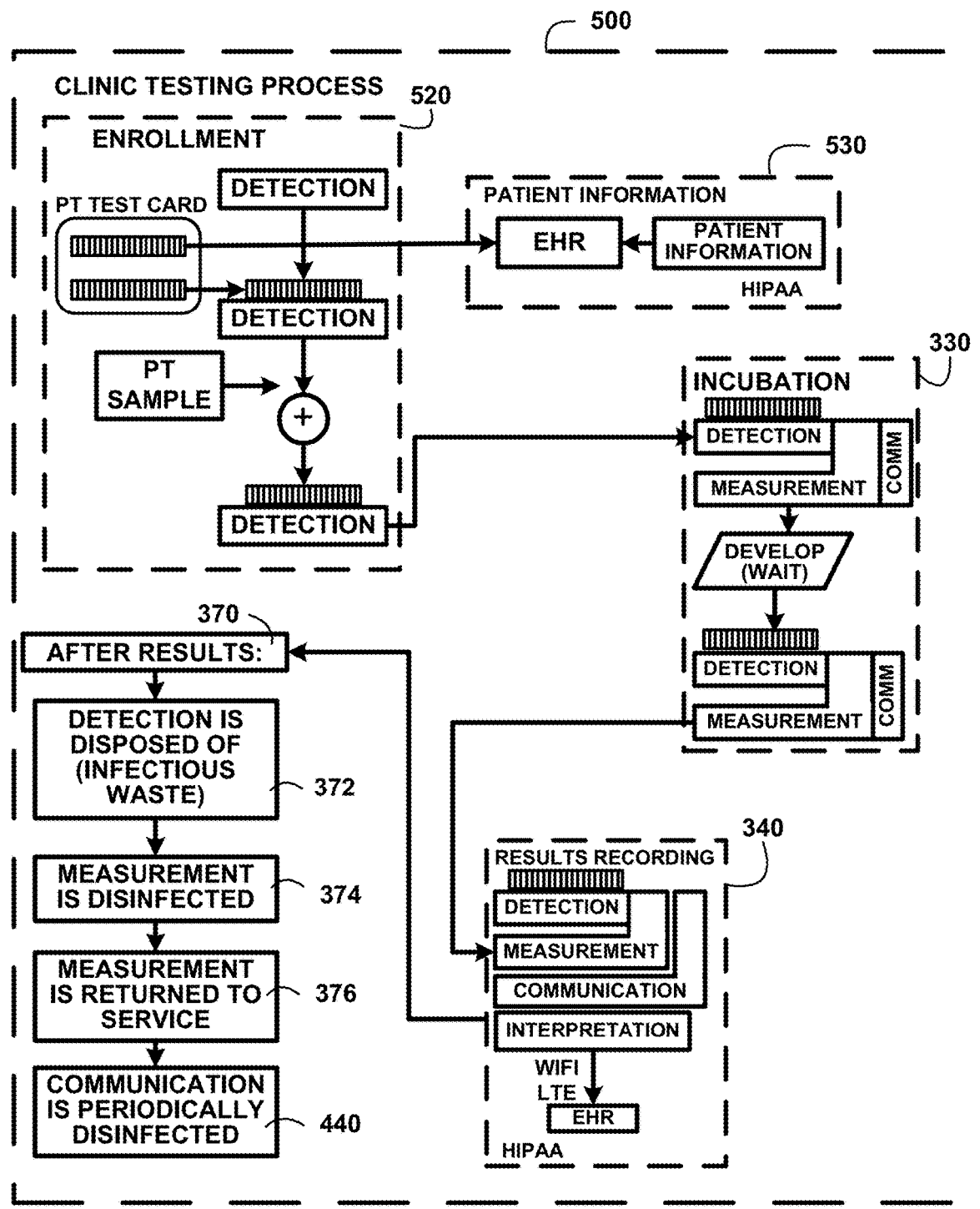
FIG. 5 shows for illustrative purposes only an example of a clinic testing process of one embodiment.

A Clinic Testing Process:

FIG. 5 shows for illustrative purposes only an example of a clinic testing process of one embodiment. FIG. 5 shows a clinic testing process 500 an enrollment 520 of patients being testing and issuing a patient test card. The patient test card assigns a unique identifying testing code and records patient information 530 on the card. The patient card is used for transmitting to the patient EHR the patient information and testing results according to HIPAA.

The process includes detection where the detection with patient ID is first performed prior to placing a patient sample. After placing the patient sample detection with patient ID proceeds to incubation 330 of the patient sample with heat applied to the sample. The detection with patient ID is followed with a measurement of the electrode impedance after a predetermined "develop" time period of the incubated patient sample.

Results recording 340 is performed after the detection with patient ID measurement is transmitted with communication to the interpretation means. The results recording 340 after interpretation is transmitted via WIFI LTE to the patient EHR under HIPAA. After results: 370 are recorded detection is disposed of (infectious waste) 372, measurement is disinfected 374, measurement is returned to service 376, and communication is periodically disinfected 440 of one embodiment.

Figure 6:
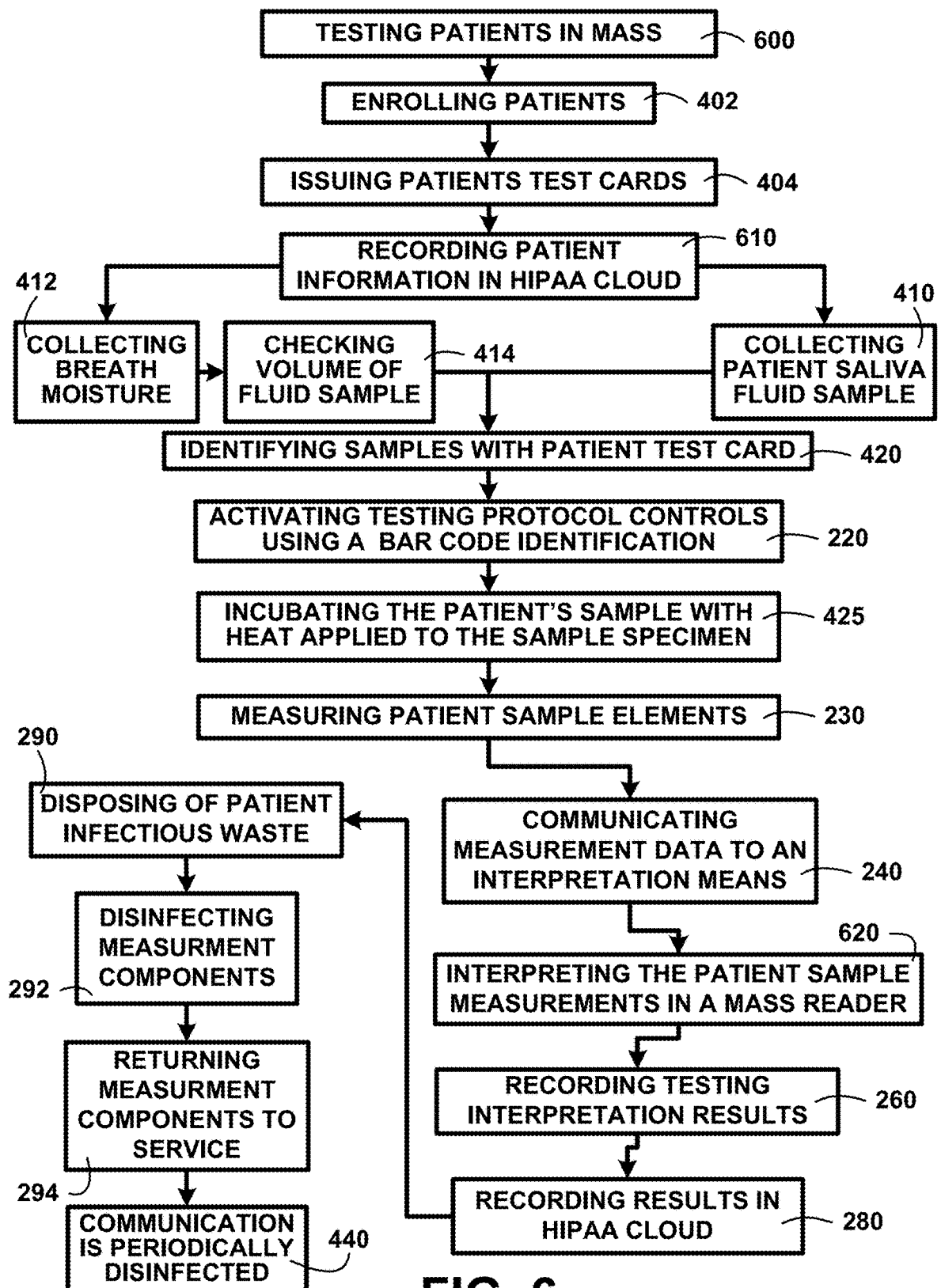
FIG. 6 shows a block diagram of an overview flow chart of testing patients in mass of one embodiment.

Testing Patients in Mass:

FIG. 6 shows a block diagram of an overview flow chart of testing patients in mass of one embodiment. FIG. 6 shows testing patients in mass 600 using the electrochemical sensing platform devices and processes 100 of FIG. 1. A process is used for enrolling patients 402 and issuing patients test cards 404. The patients test cards include a unique testing code and patient information. The processing includes recording patient information on a HIPAA cloud 610.

The processing continues with collecting patient saliva fluid sample 410 testing specimen. In another embodiment the process is collecting breath moisture 412 from a patient and checking volume of breath fluid sample 414. Collecting patient samples includes identifying samples with patient test card 420. Processing continues with activating testing protocol controls using at least one identification digital memory device 220. A process is used for incubating the patient's sample with heat applied to the sample specimen 425. After incubation a process is used for measuring patient oral fluid sample impedance 230 of the detection electrode. Processing for communicating measurement data to an interpretation means 240 for interpreting the patient sample measurements in a mass reader 620 and recording testing interpretation results 260. Recording testing interpretation results 260 includes recording results on a HIPAA cloud 280. After the results are recorded the process continues with disposing of patient infectious waste 290, disinfecting measurement components 292, returning measurement components to service 294, and communication is periodically disinfected 440 of one embodiment.

Figure 7:
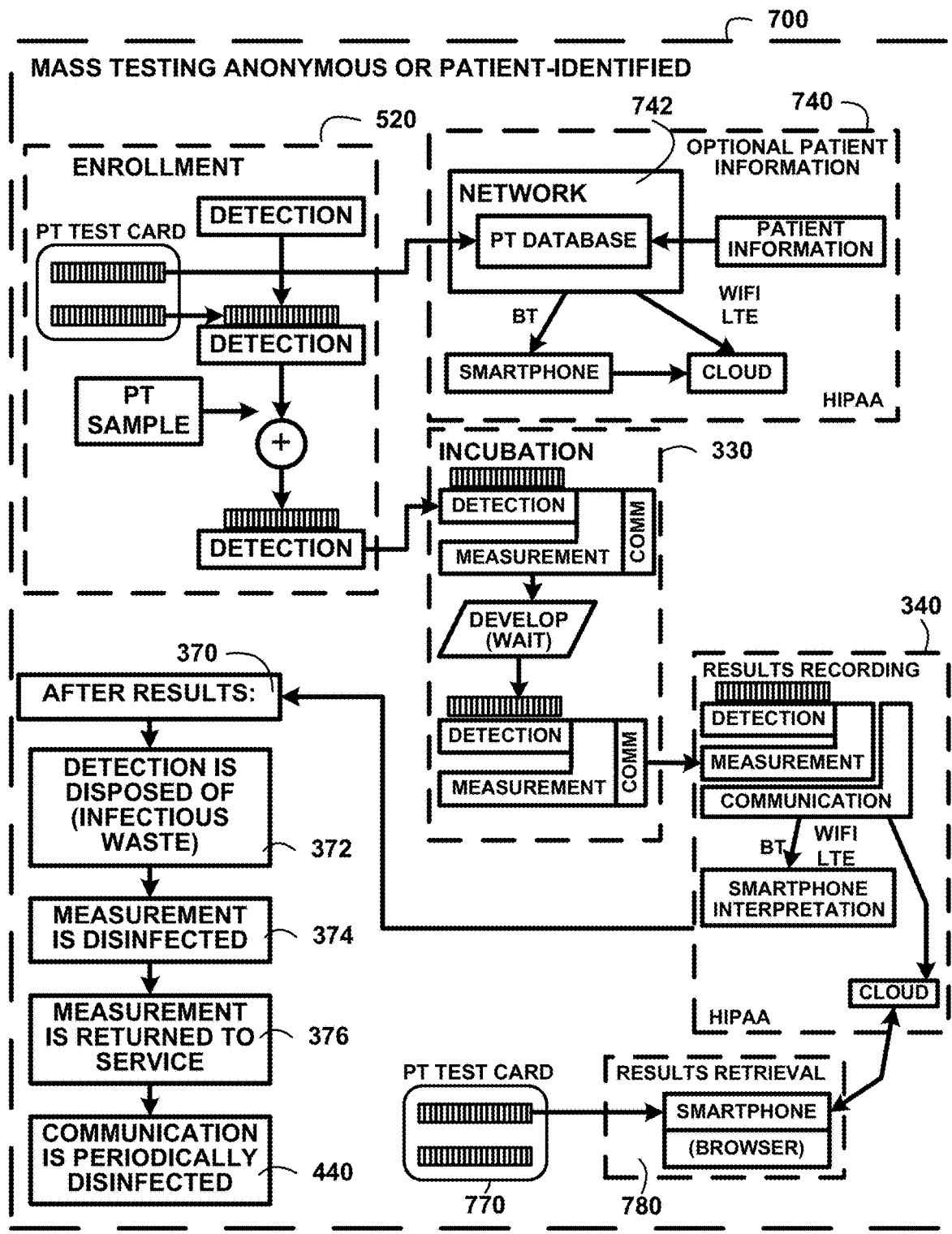
FIG. 7 shows for illustrative purposes only an example of mass testing anonymously or patient-identified of one embodiment.

Mass Testing Anonymously or Patient-Identified:

FIG. 7 shows for illustrative purposes only an example of mass testing anonymously or patient-identified of one embodiment. FIG. 7 shows mass testing anonymously or patient-identified 700. Mass testing processing begins with enrollment 520 of patients and issuing a patient test card to each patient. The patient test card includes optional patient information 740 that may be transmitted to a network 742 and recorded on a patient database. The optional patient information 740 may be transmitted to BT smartphone for accessing patient information transmitted via WIFI LTE to a HIPAA cloud.

Detection with a patient ID labeled patient sample is followed by incubation 330 with applied heat to develop for a predetermined time period the patient sample. Detection with a patient ID sample after developing is then processed for measurement of electrode impedance. The detection measurement results recording 340 is communicated using a communication device to an interpretation system for determination of the concentration of any detected virus or bacterial pathogen.

The interpretation results are transmitted via BT smart phone and WIFI LTE to a patient EHR HIPAA file. A patient test ID card 770 is used by a patient who logs in to a HIPAA cloud for results retrieval 780 using a smartphone/browser. After results: 370 are recorded detection is disposed of (infectious waste) 372, measurement is disinfected 374, measurement is returned to service 376, and communication is periodically disinfected 440 of one embodiment.

Figure 8:
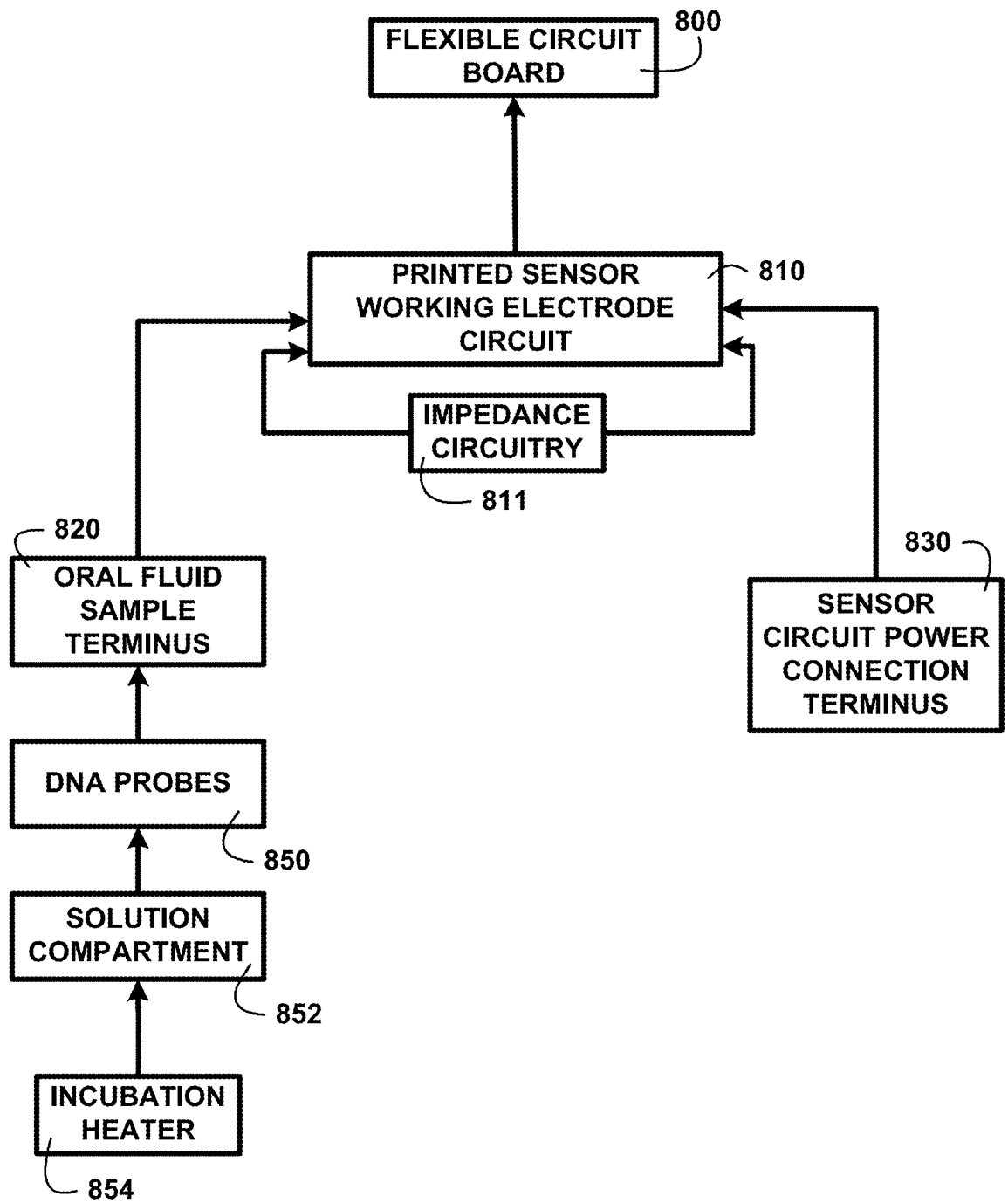
FIG. 8 shows a block diagram of an overview of a printed sensor electrode circuit of one embodiment.

A Printed Sensor Electrode Circuit:

FIG. 8 shows a block diagram of an overview of a printed sensor electrode circuit of one embodiment. FIG. 8 shows a flexible circuit board 800 with a printed sensor working electrode circuit 810 deposited on the surface. The printed sensor electrode circuit 810 can be made using printers including an ink jet printer and a 3D printer. The electrode is composed of an electrically conductive material of one embodiment.

The printed sensor electrode impedance circuitry 811 is configured with an oral fluid sample terminus 820. The oral fluid sample terminus 820 includes DNA probes 850 that will be in contact with the patient oral fluid sample with placed. A solution compartment 852 is coupled over the DNA probes 850 for receiving an oral fluid sample. An incubation heater 854 is placed under the solution compartment 852. The opposite end of the printed sensor working electrode circuit 810 includes a sensor circuit power connection terminus 830 for connecting a power source of one embodiment.

Figure 9:
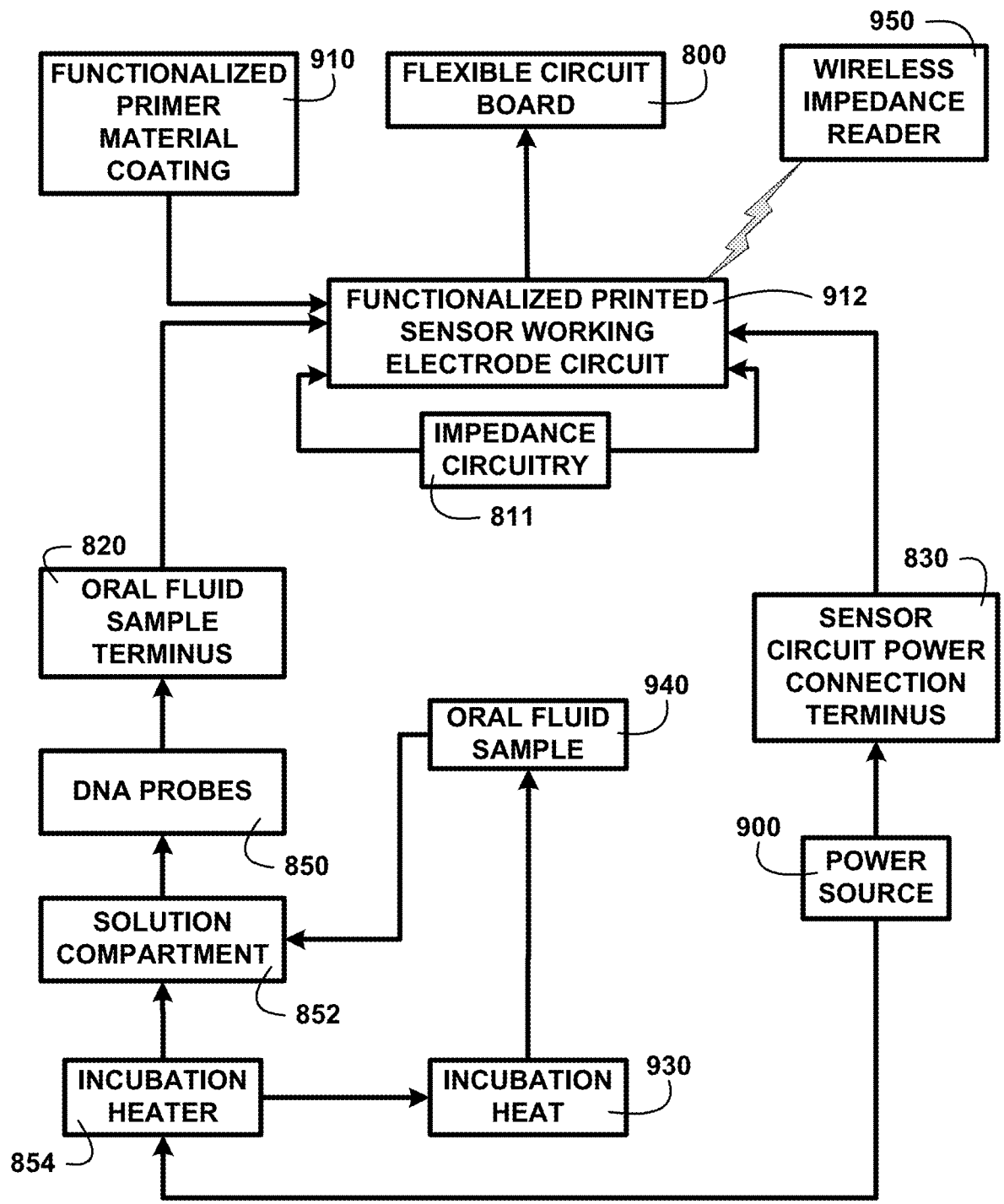
FIG. 9 shows a block diagram of an overview of a functionalized printed sensor working electrode circuit of one embodiment.

A Functionalized Printed Sensor Working Electrode Circuit:

FIG. 9 shows a block diagram of an overview of a functionalized printed sensor working electrode circuit of one embodiment. FIG. 9 shows the flexible circuit board 800, printed sensor working electrode circuit 810, impedance circuitry 811, oral fluid sample terminus 820, DNA probes 850, solution compartment 852, incubation heater 854 and sensor circuit power connection terminus 830.

A functionalized primer material coating 910 is deposited on the surface of the printed sensor working electrode circuit 810 to form a functionalized printed sensor working electrode circuit 912. An oral fluid sample 940 is shown placed in the solution compartment 852 and contacting the DNA probes 850. A power source 900 is coupled to the sensor circuit power connection terminus 830 for providing power to the incubation heater 854 for incubation heat 930 to the oral fluid sample 940 during incubation of one embodiment. The power source 900 also provides power for impedance testing that is read using a wireless impedance reader 950 of one embodiment.

Figure 10:
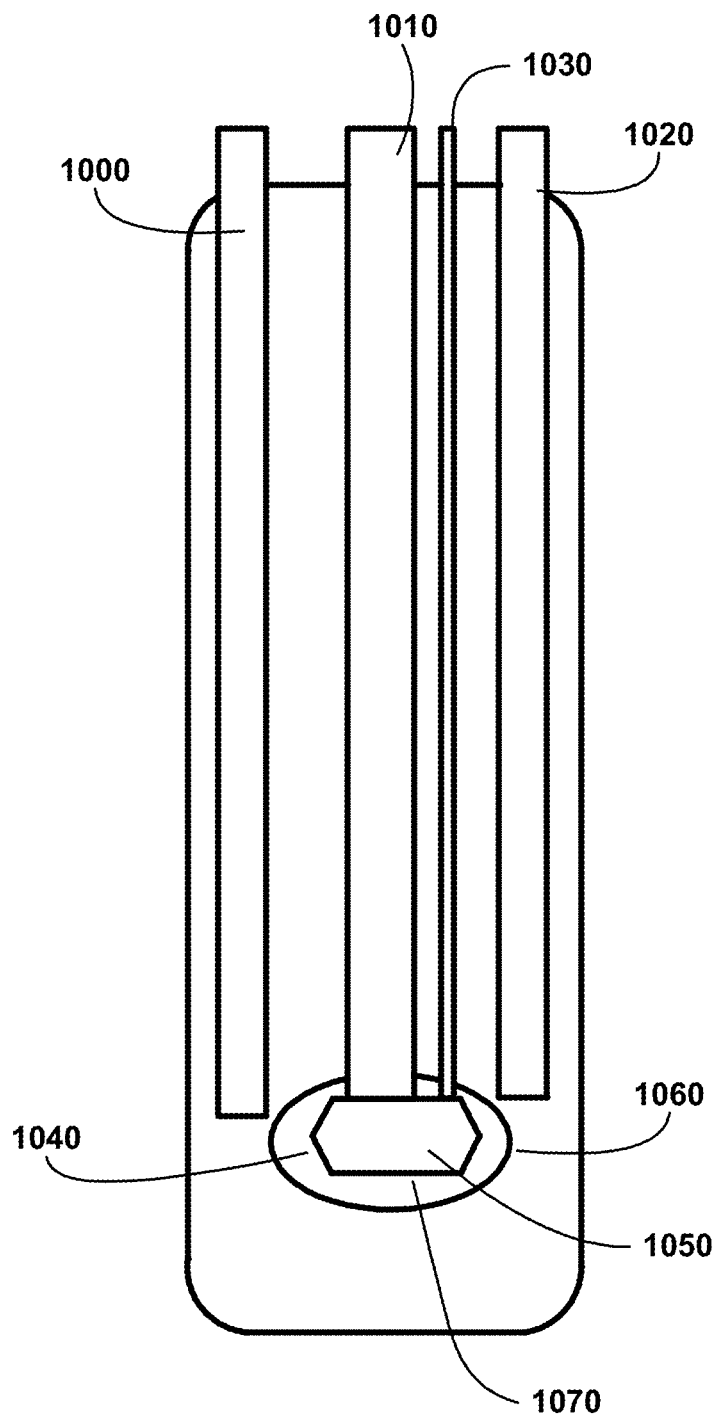
FIG. 10 shows for illustrative purposes only an example of an incubation heater of one embodiment.

An Incubation Heater:

FIG. 10 shows for illustrative purposes only an example of an incubation heater of one embodiment. FIG. 10 shows a heater below working electrode head 1050 that is used for heating a patient oral fluid sample during incubation. In one embodiment the detection device includes a reference electrode 1000, working electrode 1010, and counter electrode 1020. The working electrode head 1060 is shown coupled to a heated fluid tube 1030.

A solution compartment 1070 is used for placing the patient oral fluid sample. The solution compartment can be located in the side wall next to the head of the working electrode separated by a thin film that melts away or directly above the working electrode such that when the sample is placed in the hole from above the heater then melts the top membrane so the sample mixes then the bottom member melts, allowing the mixed sample to pour down on the working electrode surface 1040. All body fluids will be able to be tested however; different test strips will need different combinations of fluid and heat or none at all of one embodiment.

Figure 11A:
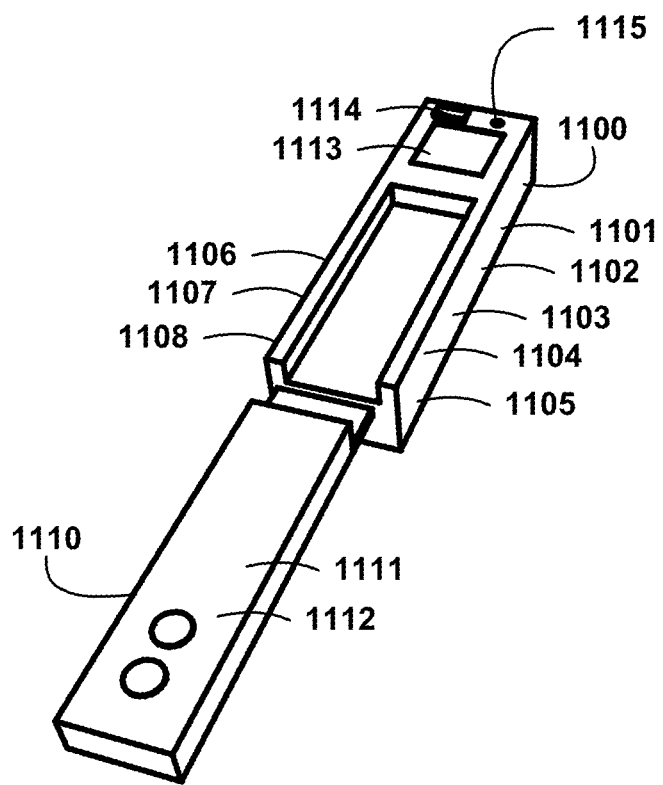
FIG. 11A shows for illustrative purposes only an example of a detection cartridge of one embodiment.

A Detection Cartridge:

FIG. 11A shows for illustrative purposes only an example of a detection cartridge of one embodiment. FIG. 11A shows an electrochemical sensing platform device 1100 including a processor 1101, at least one internal and external power source 1102, at least one communication device 1103, and at least one digital memory device 1104. The electrochemical sensing platform device 1100 is configure to include an impedance measuring device 1105, an interpretation processor 1106, at least one data cartridge reader 1107, and at least one testing protocol controls digital memory Identification activator 1108. The electrochemical sensing platform device 1100 includes a testing status display 1113 for displaying the testing process status and results. An on/off and selection button 1114 is used for turning on the power which is shown in a power off indicator light 1115 condition. At least one detection cartridge 1110 includes at least one functionalized printed electrode 1111 and an incubation heater 1112 of one embodiment.

Figure 11B:
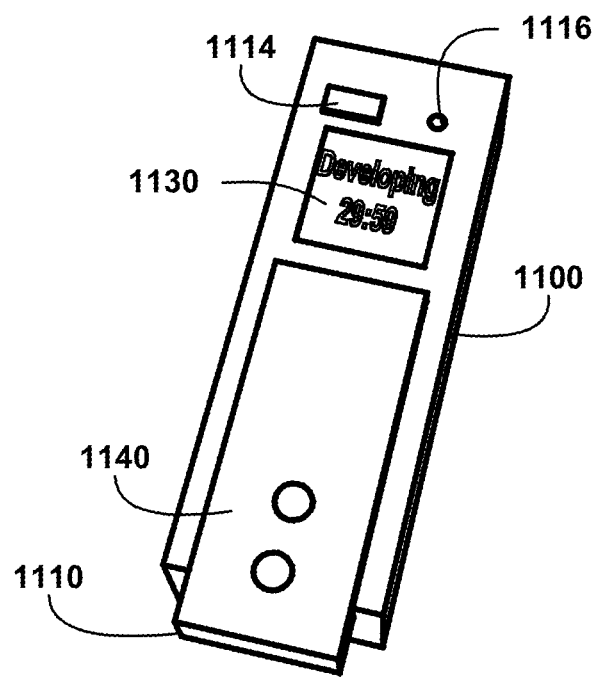
FIG. 11B shows for illustrative purposes only an example of a detection device of one embodiment.

A Detection Device:

FIG. 11B shows for illustrative purposes only an example of a detection device of one embodiment. FIG. 11B shows electrochemical sensing platform device 1100 includes at least one detection cartridge 1110 and an on/off and selection button 1114. In this instance the power on indicator light 1116 are lite indicating the power has been turned on. A detection cartridge inserted into the electrochemical sensing platform 1140 produces a testing status display showing developing 29.59 1130 of one embodiment.

Figure 12A:
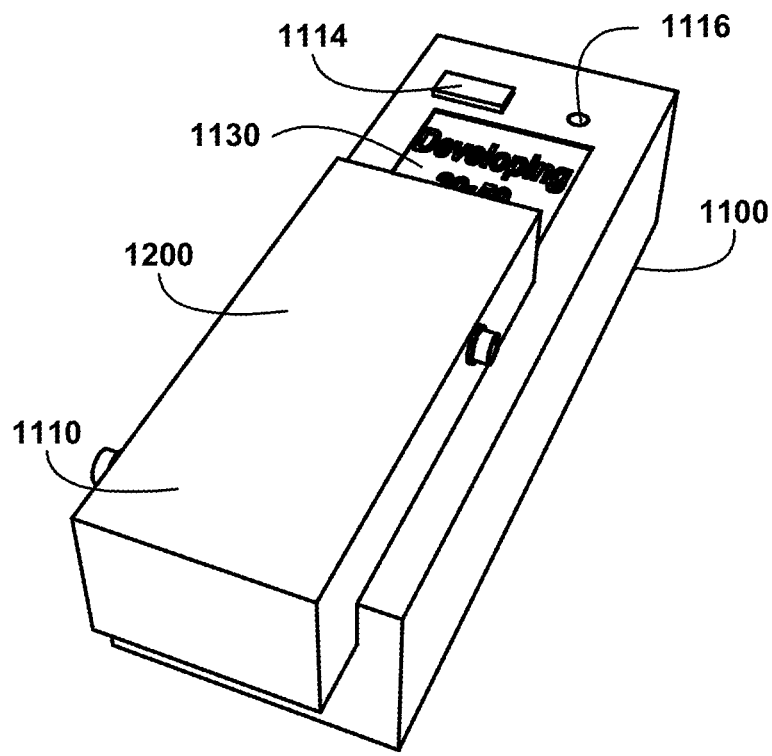
FIG. 12A shows for illustrative purposes only an example of a detection device display developing of one embodiment.

A Detection Device Display Developing:

FIG. 12A shows for illustrative purposes only an example of a detection device display developing of one embodiment. FIG. 12A shows the electrochemical sensing platform device 1100, at least one detection cartridge 1110, on/off and selection button 1114, power on indicator light 1116, testing status display showing developing 29.59 1130 in a high fluid volume detection cartridge 1200 of one embodiment.

Figure 12B:
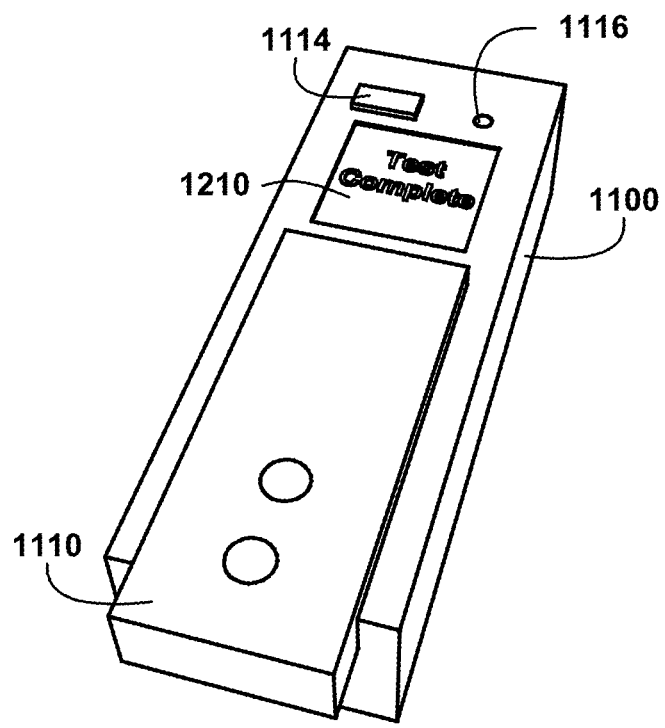
FIG. 12B shows for illustrative purposes only an example of a detection device display test complete of one embodiment.

A Detection Device Display Test Complete:

FIG. 12B shows for illustrative purposes only an example of a detection device display test complete of one embodiment. FIG. 12B shows the electrochemical sensing platform device 1100, at least one detection cartridge 1110, on/off and selection button 1114, and power on indicator light 1116. A testing status display showing test complete 1210 and the end of a testing process cycle of one embodiment.

Figure 13:
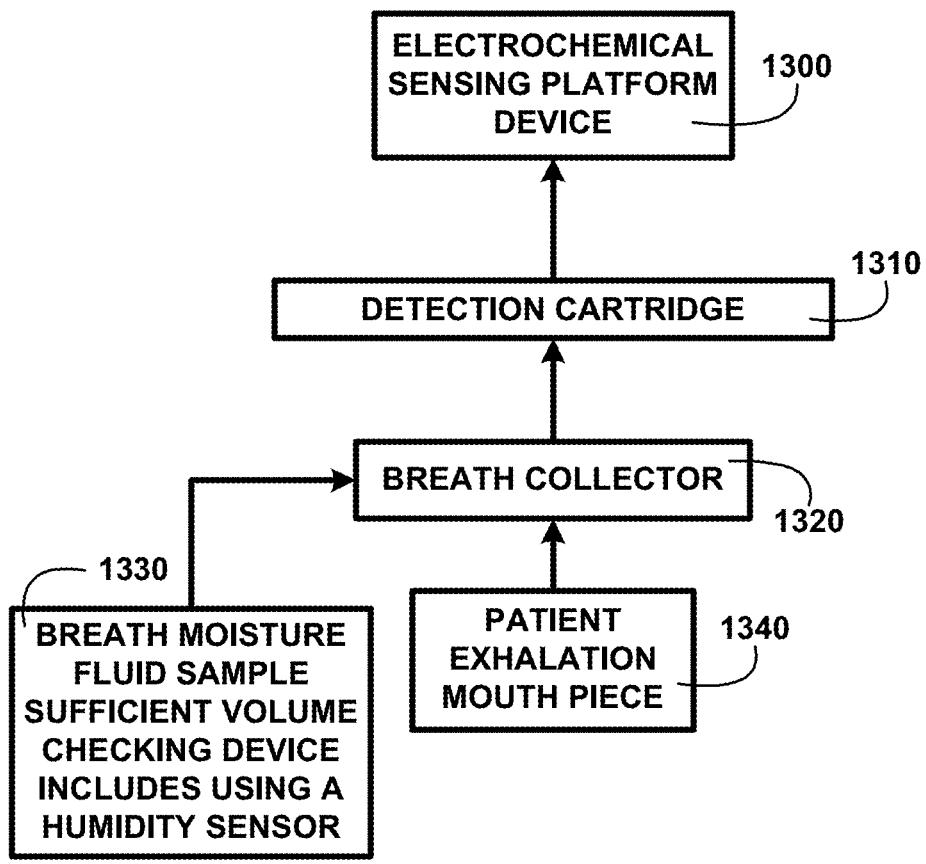
FIG. 13 shows a block diagram of an overview of a detection cartridge breath collector of one embodiment.

A Detection Cartridge Breath Collector:

FIG. 13 shows a block diagram of an overview of a detection cartridge breath collector of one embodiment. FIG. 13 shows in another embodiment an electrochemical sensing platform device 1300. Coupled to the electrochemical sensing platform device 1300 is a detection cartridge 1310. The detection cartridge 1310 is configured with a patient exhalation mouth piece 1340. The patient exhalation mouth piece 1340 is coupled to a breath collector 1320. The breath collector 1320 is used to collect moisture in the exhaled air of the patient. The breath collector 1320 includes a breath moisture fluid sample sufficient volume checking device includes using a humidity sensor 1330. A patient may need to exhale a number of times to allow collection of sufficient moisture to perform the testing of one embodiment.

Figure 14:
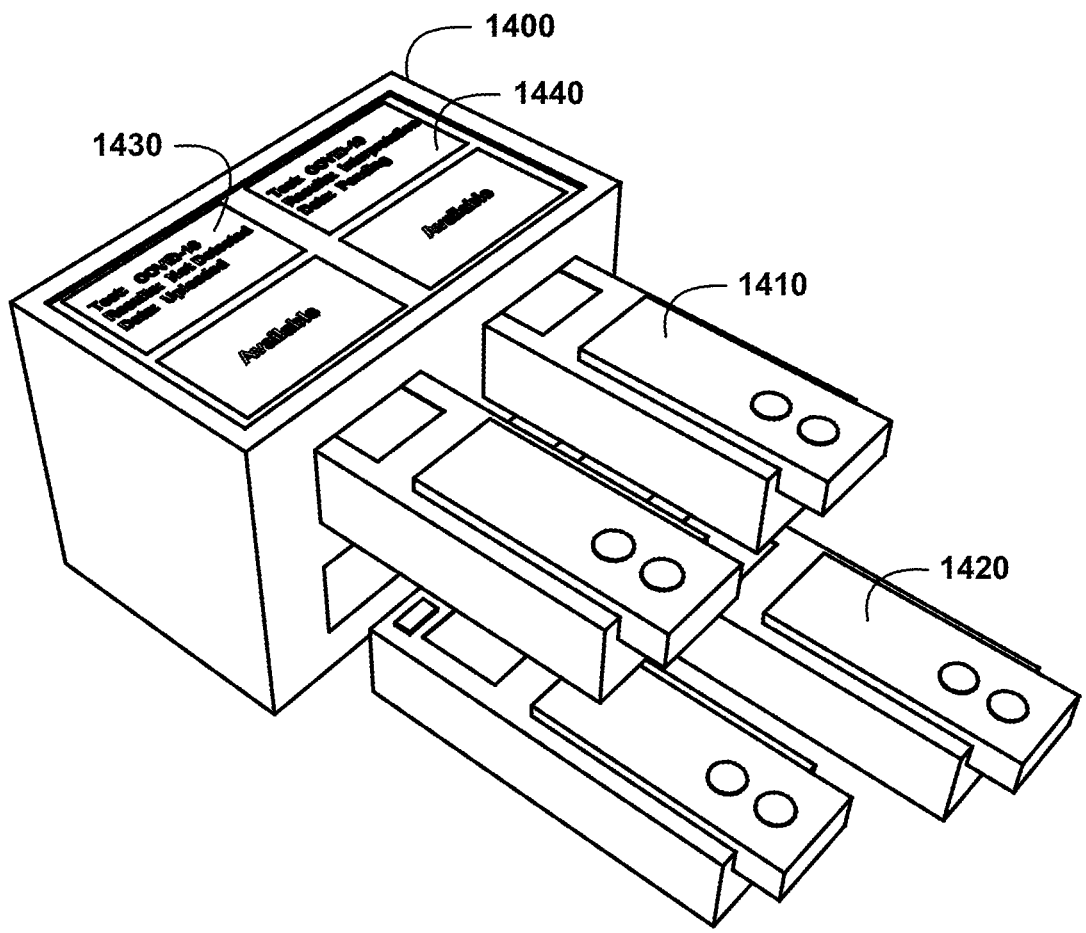
FIG. 14 shows for illustrative purposes only an example of a multi-reader of one embodiment.

A Multi-Reader:

FIG. 14 shows for illustrative purposes only an example of a multi-reader of one embodiment. FIG. 14 shows a multi detection device reader 1400. The multi detection device reader 1400 is shown with at least one detection device inserted into the multi detection device reader 1410. Also showing is at least one detection device not inserted into the multi detection device reader 1420. The multi detection device reader 1400 includes test results displays. In this instance one test results display showing uploaded 1430 and the other test results display showing pending 1440 of one embodiment.

Figure 15:
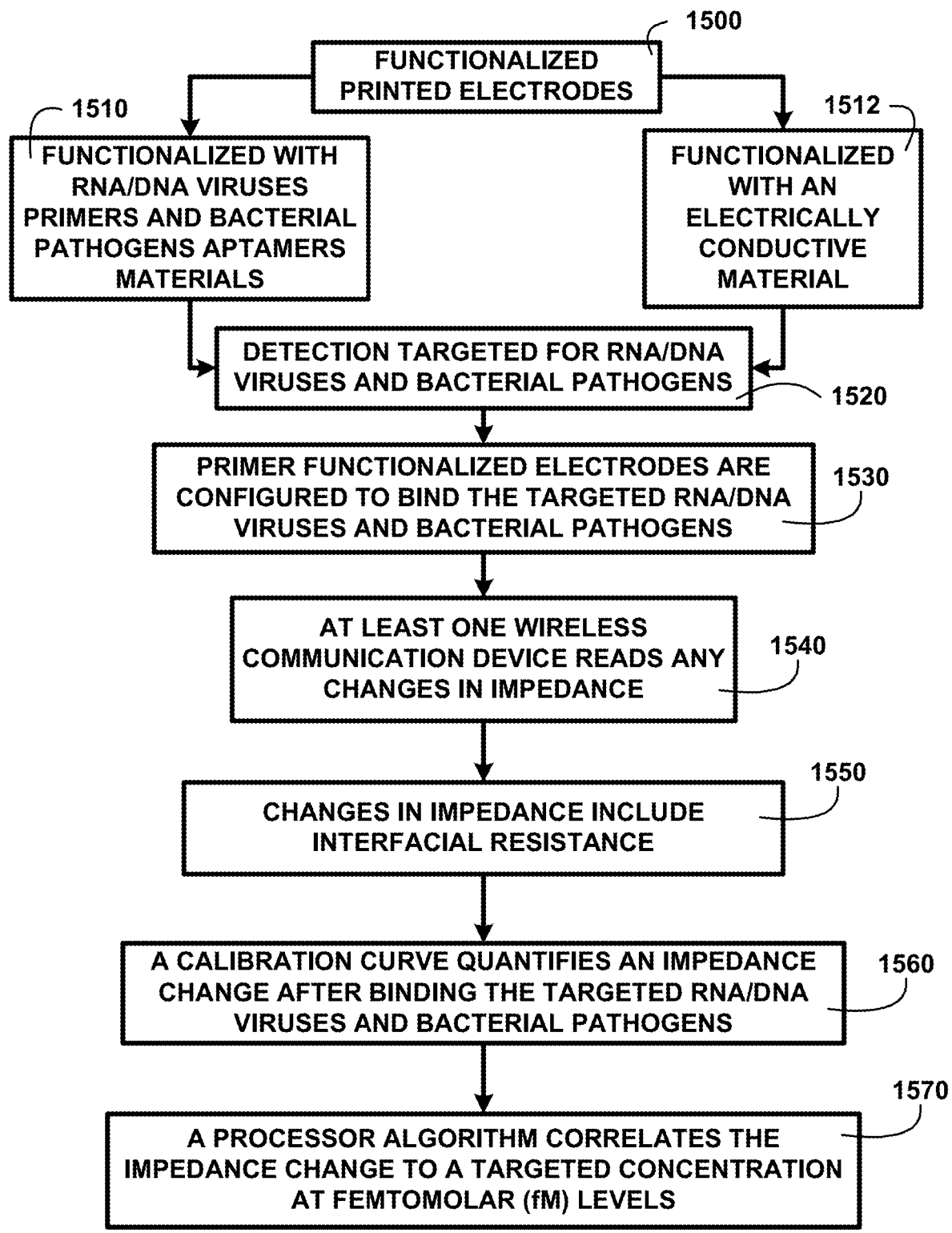
FIG. 15 shows a block diagram of an overview of functionalized printed electrodes of one embodiment.

Functionalized Printed Electrodes:

FIG. 15 shows a block diagram of an overview of functionalized printed electrodes of one embodiment. FIG. 15 shows functionalized printed electrodes 1500. The functionalized printed electrodes 1500 are functionalized with RNA/DNA virus primers and bacterial pathogens aptamers materials 1510. In another embodiment printed electrodes 1500 are functionalized with an electrically conductive material 1512. The DNA probes 850 of FIG. 8B consist of materials corresponding to the specific RNA/DNA viruses and bacterial pathogens primers and aptamer materials. The functionalized printed electrodes 1500 are configured for detection targeted for RNA/DNA viruses and bacterial pathogens 1520.

Primer functionalized electrodes are configured to bind the targeted RNA/DNA viruses and bacterial pathogens 1530 to the probes and aptamers. At least one wireless communication device reads any changes in impedance 1540 and records any changes for transmission to an interpretation means. Changes in impedance include interfacial resistance 1550. A calibration curve quantifies an impedance change after binding the targeted RNA/DNA viruses and bacterial pathogens 1560. A processor algorithm correlates the impedance change to a targeted concentration at femtomolar (fM) levels 1570 of one embodiment.

Electrode Binding of Targeted RNA/DNA Viruses and Bacterial Pathogens:

FIG. 16 shows a block diagram of an overview of an example of electrode binding of targeted RNA/DNA viruses and bacterial pathogens of one embodiment. FIG. 16 shows the electrochemical detection device for COVID-19 SARS-CoV-2 virus in saliva 1600. An inkjet nozzle deposits an electrically conductive electrode material 1604 on a Polymide flexible substrate 1640 to make an inkjet-printed sensor electrode 1610. A DNA primer coating specific for SARS-CoV-2 is bound to the electrically conductive electrode 1620 to form a functionalized printed electrode. Coupled to the inkjet-printed sensor electrode 1610 are an external power source 1613 and an internal power source 1612. Also coupled to the inkjet-printed sensor electrode 1610 is a solution compartment 1615 the receiver for the saliva sample 1617.

An incubation heater 1614 is coupled underneath the solution compartment 1615. The internal power source 1612 is shown connected to the incubation heater 1614 for applying heat to the saliva sample during the predetermined incubation time period. During incubation the SARS-CoV-2 is bound to the electrically conductive electrodes with DNA primer 1622. Each terminus of the sensor electrode forms a measurement circuit for processing an impedance measurement 1650. The impedance measurement 1650 is read with a WIFI transmission to a smart phone 1660. Interpretation is processed on a sensing platform smart phone app on a patient smart phone 1670. The testing results displayed on a sensing platform smart phone app 1680 let the patient know quickly if they are infected with the COVID-19 SARS-CoV-2 virus of one embodiment.

Figure 17:
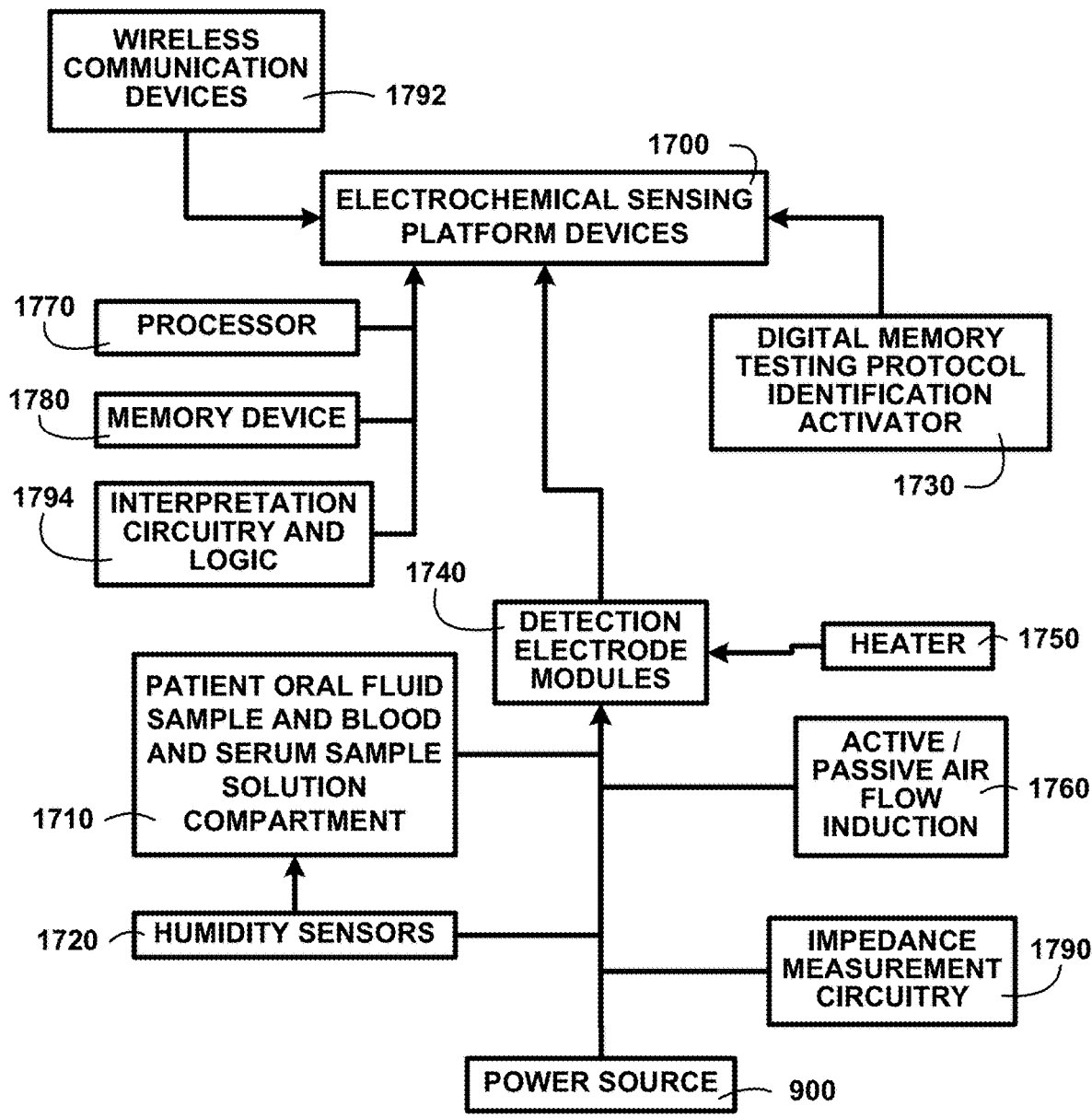
FIG. 17 shows a block diagram of an overview of electrochemical sensing platform devices of one embodiment.

Electrochemical Sensing Platform Devices:

FIG. 17 shows a block diagram of an overview of electrochemical sensing platform devices of one embodiment. FIG. 17 shows electrochemical sensing platform devices 1700 that are configured with wireless communication devices 1792, at least one processor 1770, memory device 1780, interpretation circuitry and logic 1794, and impedance measurement circuitry 1790. Detection electrode modules 1740 are inserted into the electrochemical sensing platform devices 1700 for reading and interpretation of the detection testing. Coupled to the detection electrode modules 1740 are a patient oral fluid sample and blood and serum sample solution compartment 1710, and humidity sensors 1720. Also coupled to the detection electrode modules 1740 are at least one digital memory testing protocol Identification activator 1730, heater 1750, and active/passive air flow induction 1760. Another element coupled to the detection electrode modules 1740 is a power source 900 of one embodiment.

Figure 18A:
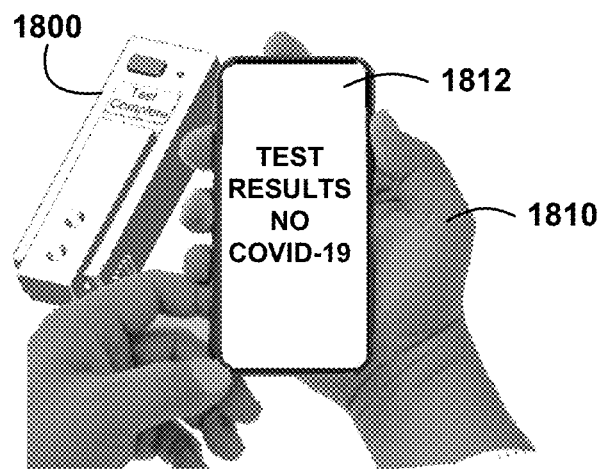
FIG. 18A shows for illustrative purposes only an example of home use application environment of one embodiment.
Figure 18B:
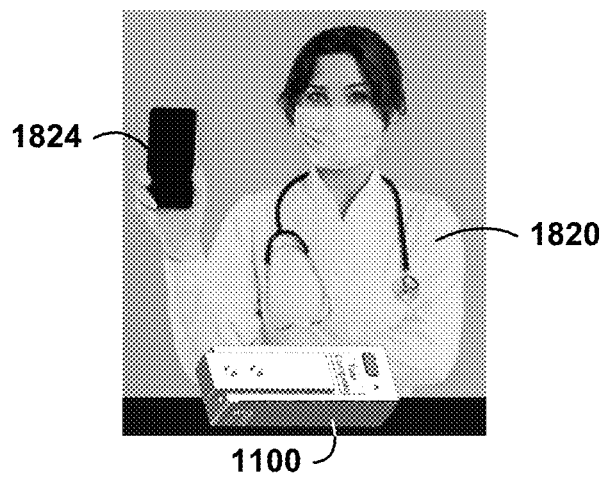
FIG. 18B shows for illustrative purposes only an example of clinic use application environment of one embodiment.
Figure 18C:
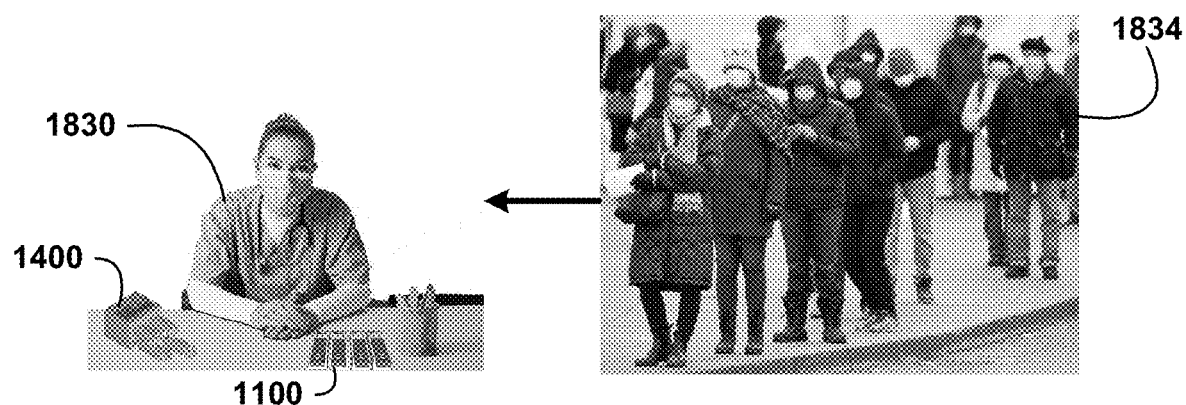
FIG. 18C shows for illustrative purposes only an example of mass use application environment of one embodiment.

Application Environments:

FIGS. 18A, 18B and 18C shows application environments for use of the electrochemical sensing platform devices and processes 100 of FIG. 1.

FIG. 18A shows for illustrative purposes only an example of home use application environment of one embodiment. FIG. 18A shows in one embodiment the electrochemical sensing platform devices and processes 100 of FIG. 1 are configured for home use with an untrained user, following written instructions 1810. The home use processing of the electrochemical sensing platform device 1800 with detection, measurement and interpretation means reported to user via a sensing platform smart phone app 1812 that in this instance reports "Test Results no Covid-19".

FIG. 18B shows for illustrative purposes only an example of clinic use application environment of one embodiment. FIG. 18B shows in another embodiment Clinical Use with a semi-trained user 1824, having previously performed the test and follows written instructions 1820. Processing includes electrochemical sensing platform device 1100 with detection, measurement and test data transmitted over WIFI to a network for reading and interpretation and reporting results on a sensing platform smart phone app in this instance waiting for the results report to be displayed.

FIG. 18C shows for illustrative purposes only an example of mass use application environment of one embodiment. FIG. 18C shows in yet another embodiment Mass Use with a trained operator 1830, repeatedly performing the tests from documented procedures, conversant in test sampling and preparation techniques. Mass Use utilizes an electrochemical sensing platform device 1100 with detection, measurement and using an external multiple device multi reader and interpretation device 1400. The multiple device multi reader and interpretation device 1400 facilitates processing test of a large number of people 1834 in a short period of time.

Figure 19:
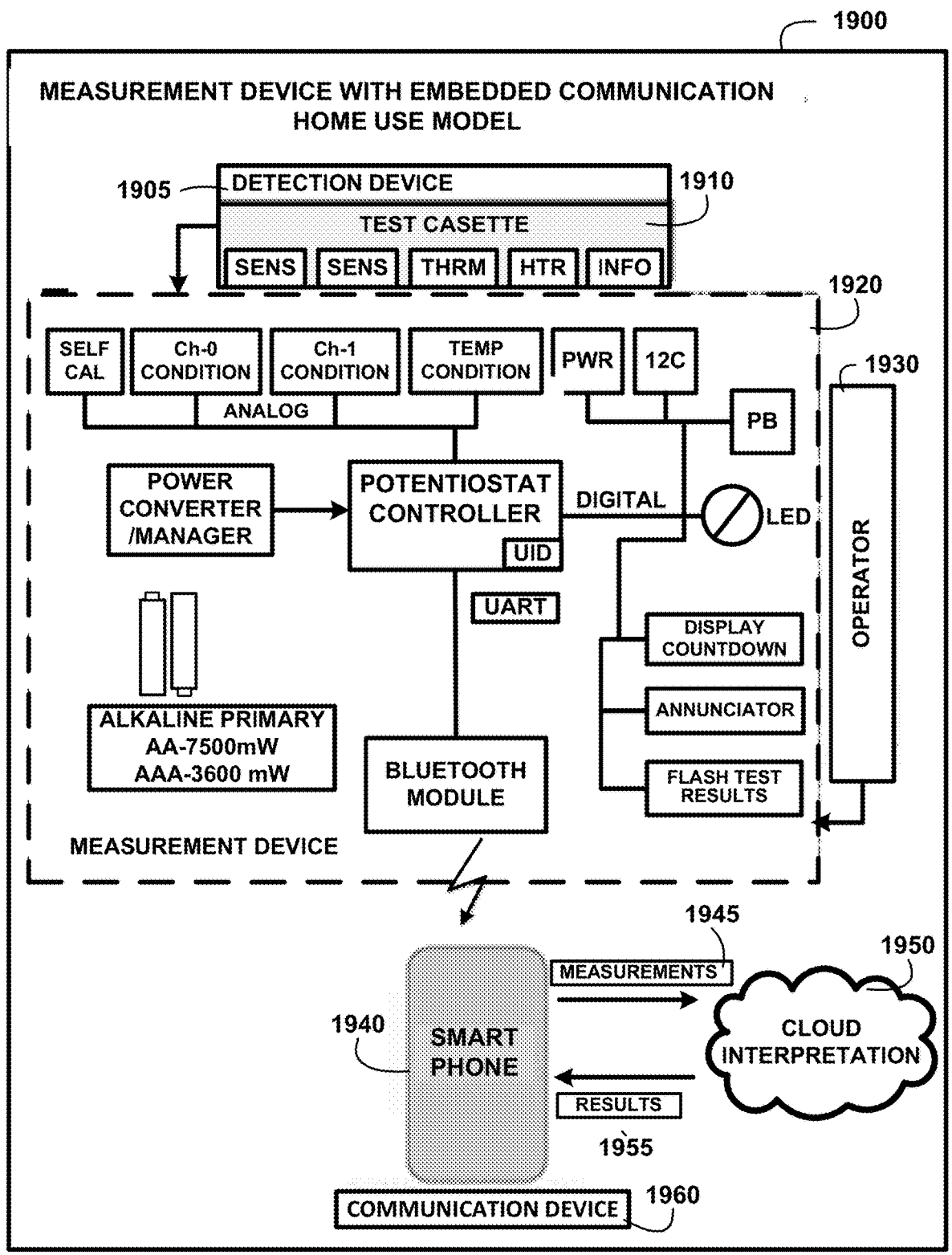
FIG. 19 shows for illustrative purposes only an example of a measurement device with embedded communication home use model of one embodiment.

A Measurement Device with Embedded Communication Home Use Model:

FIG. 19 shows for illustrative purposes only an example of a measurement device with embedded communication home use model of one embodiment. FIG. 19 shows an example of a measurement device with embedded communication home use model 1900. The home use model includes a detection device 1905 with a test cassette 1910 with modules for SENS, SENS, THRM, HTR, and INFO. A measurement device 1920 is configured with PWR, 12C, PB and an LED. The measurement device 1920 includes operations of a display countdown, annunciator and flash test results. An operator 1930 turns on and off and makes selections of the operations of the home use model. The measurement device 1920 includes analog operations for self cal (calibration), Ch-0 condition, Ch-1 condition, and temp condition. The measurement device 1920 includes a potentiostat controller UID, power converter/manager for alkaline primary AA-7500 mW and AAA-3600 mW batteries, digital devices. UART and Bluetooth module. The Bluetooth module communicates with at least one communication device 1960 including a smart phone 1940 for transmitting and receiving data including measurements 1945, cloud (interpretation) 1950 and results 1955 of one embodiment.

Figure 20:
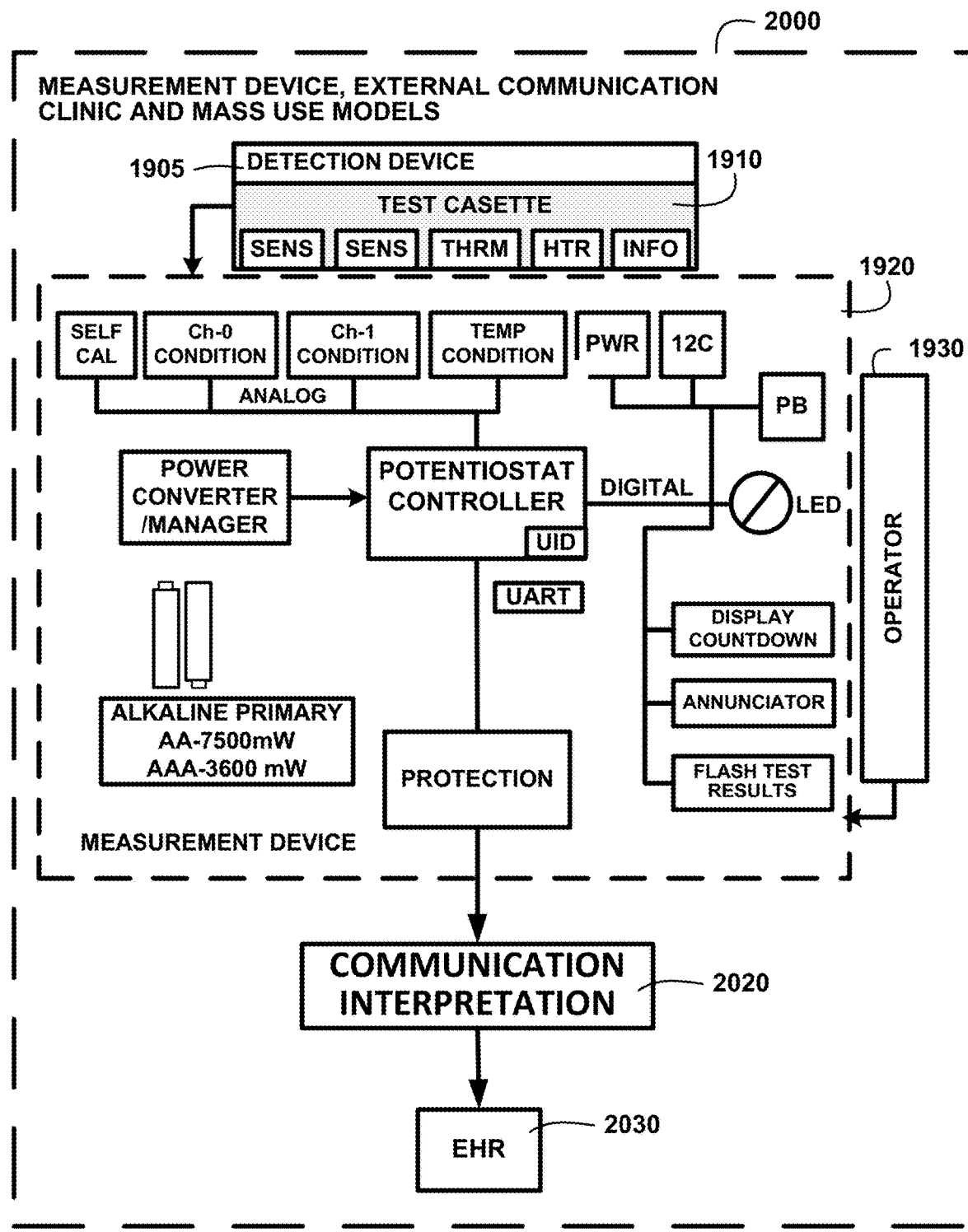
FIG. 20 shows for illustrative purposes only an example of a measurement device, external communication clinic and mass use models of one embodiment.

A Measurement Device, External Communication Clinic and Mass Use Models:

FIG. 20 shows for illustrative purposes only an example of a measurement device, external communication clinic and mass use models of one embodiment. FIG. 20 shows an example of a measurement device, external communication clinic and mass use models 2000. The clinic and mass use models include a detection device 1905 with a test cassette 1910 with modules for SENS, SENS, THRM, HTR, and INFO.

A measurement device 1920 is configured with PWR, 12C, PB and an LED. The measurement device 1920 includes operations of a display countdown, annunciator and flash test results. An operator 1930 turns on and off and makes selections of the operations of the home use model. The measurement device 1920 includes analog operations for self cal (calibration), Ch-0 condition, Ch-1 condition, and temp condition.

The measurement device 1920 includes a potentiostat controller UID, power converter/manager for alkaline primary AA-7500 mW and AAA-3600 mW batteries, digital devices. UART and protection. Communication interpretation 2020 is performed on external devices wherein the detection and measurement data is communicated to a network for interpretation. The interpretation results are transmitted to a patient EHR 2030 of one embodiment.

Figure 21:
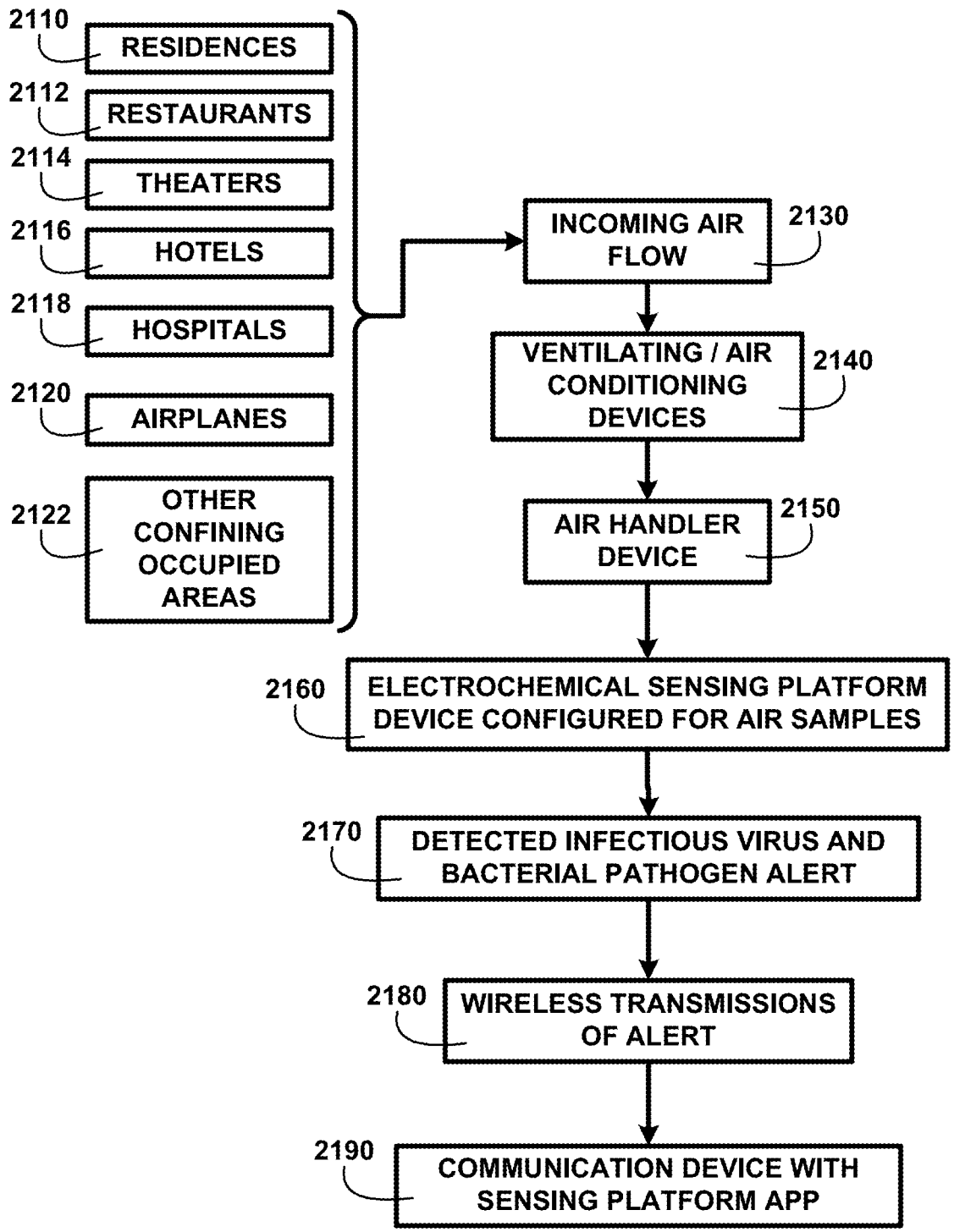
FIG. 21 shows a block diagram of an overview of electrochemical air sampling sensing platform devices of one embodiment.

Electrochemical Air Sampling Sensing Platform Devices:

FIG. 21 shows a block diagram of an overview of electrochemical air sampling sensing platform devices of one embodiment. FIG. 21 shows areas where people congregate frequently including residences 2110, restaurants 2112, theaters 2114, hotels 2116, hospitals 2118, airplanes 2120, and other confining occupied areas 2122.

One commonality of these locations is the ventilating of the indoor air. Incoming air flow 2130 to ventilating/air conditioning devices 2140 is passed through the rooms and other occupied areas by the ventilating/air conditioning devices 2140 air handler device 2150. The testing of this air can detect the presence of infectious viruses and bacterial pathogens including SARS-CoV-2 and other viruses, MSRA, Legionnaires770830 and other infectious microorganisms.

In one embodiment an electrochemical sensing platform device configured for air samples 2160 will test the air as it passes through the electrochemical sensing platform device configured for air samples 2160. The electrochemical sensing platform device configured for air samples 2160 will be placed within the air flow.

Should the electrochemical sensing platform device detect any infectious viruses and bacterial pathogens in the air the device will broadcast a detected infectious virus and bacterial pathogen alert 2170. Communication devices in the electrochemical sensing platform device will initiate wireless transmissions of alert 2180 to a user communication device with sensing platform app 2190 so they can take appropriate actions of one embodiment.

The foregoing has described the principles, embodiments and modes of operation of the present invention. However, the invention should not be construed as being limited to the particular embodiments discussed. The above described embodiments should be regarded as illustrative rather than restrictive, and it should be appreciated that variations may be made in those embodiments by workers skilled in the art without departing from the scope of the present invention as defined by the following claims.

What is claimed is:

1. A method, comprising:
   making electrodes using an electrically conductive material for impedimetric detection of analytical targets in electrochemical sensing platform devices;
   printing a sensor electrode impedance circuitry with fluid sample terminus with DNA probes coupled to an oral fluid sample solution compartment for receiving fluid sample;
   collecting oral fluid sample from a patient in a solution compartment of the electrochemical sensing platform device wherein, the oral fluid sample includes collecting an oral saliva fluid sample and alternatively an exhalation moisture oral fluid sample from a patient's breath for testing;
   checking a volume of the oral fluid sample wherein, collecting may require additional patient oral saliva discharges and alternatively additional patient exhalations for accumulating a sufficient volume of the oral fluid sample;
   providing testing protocol controls for sample testing for SARS-CoV-2 virus;
   binding primers and aptamers to electrodes for functionalizing electrodes for detecting and binding targeted viruses and bacterial pathogens;
   incubating oral fluid samples in the solution compartment using a heater;
   measuring electrode impedance changes from the electrochemical sensing platform device reading of testing data and interpretation of the test data;
   recording measured electrode impedance changes in a memory device;
   integrating wireless technologies into the electrochemical sensing platform device for transmitting recorded measured electrode impedance changes; and
   providing electrochemical sensing platform device wireless transmission of interpretation of fluid sample testing using a sensing platform smart phone app on a patient's smart phone for displaying interpretation of fluid sample testing in the patient's view.

2. The method of claim 1, further comprising printing an electrode and sensor electrode impedance circuitry coupled to the electrode using a printing device including one from a group of a metallic ink jet printer and 3D printer.

3. The method of claim 1, further comprising fabricating an electrochemical sensing platform device prior to use for placing a patient saliva fluid sample in a detection device test chamber.

4. The method of claim 1, further comprising fabricating an electrochemical sensing platform device prior to use for collecting a patient's breath moisture using a breath collector coupled to the fluid sample terminus with DNA probes coupled to the solution compartment for receiving an oral fluid sample.

5. The method of claim 1, further comprising fabricating an electrochemical sensing platform device prior to use for analyzing and interpreting accurate and statistically significant impedimetric data from quantitative detection of viruses and bacterial pathogens DNA/RNA concentrations in fluid samples.

6. The method of claim 1, further comprising using an electrically conductive material for making electrodes and printed sensor electrode impedance circuitry coupled to the electrodes for performing impedimetric detection of analytical targets with measuring electrode impedance changes.

7. The method of claim 1, further comprising fabricating an electrochemical sensing platform device prior to use for collecting a patient's breath moisture using a breath collector to include the fluid sample terminus coupled to the solution compartment to a breath moisture fluid sample sufficient volume checking device includes using a humidity sensor.

8. The method of claim 1, further comprising developing the electrochemical sensing platform device to include DNA probes.

9. The method of claim 1, further comprising developing the electrochemical sensing platform devices to include DNA probes wherein viruses and bacterial pathogens RNA primers will bind to the DNA probes increasing electrical impedance.

10. The method of claim 1, further comprising developing the electrochemical sensing platform devices to include a processor, at least one detection cartridge, at least one internal and external power source, at least one communication device, at least one digital memory device, at least one impedance measuring device, an interpretation processor, and at least one data cartridge reader.

* * * * *